United States Patent [19]
Ichii et al.

[11] 3,965,165
[45] June 22, 1976

[54] PROCESS FOR PREPARING SODIUM TETROLATE

[75] Inventors: Takeshi Ichii; Hiroshi Fujita, both of Hiro, Japan

[73] Assignee: Sankyo Company Limited, Tokyo, Japan

[22] Filed: Dec. 2, 1974

[21] Appl. No.: 528,884

Related U.S. Application Data

[63] Continuation of Ser. No. 376,934, July 6, 1973, abandoned, which is a continuation of Ser. No. 145,045, May 19, 1971, abandoned, which is a continuation of Ser. No. 803,122, Feb. 27, 1969, abandoned.

[30] Foreign Application Priority Data
Mar. 4, 1968  Japan.............................. 43-15214

[52] U.S. Cl............................................. 260/533 B
[51] Int. Cl.² ......................................... C07C 51/15
[58] Field of Search ................................ 260/533 B

[56] References Cited
UNITED STATES PATENTS

| | | | |
|---|---|---|---|
| 2,605,295 | 7/1952 | Garner | 260/533 B |
| 3,541,144 | 11/1970 | Tedeschi | 260/533 B |

*Primary Examiner*—Vivian Garner
*Attorney, Agent, or Firm*—Toren, McGeady and Stanger

[57] ABSTRACT

An improved process for preparing sodium tetrolate which comprises adding methylacetylene to a mixture of a tertiary amine such as triethylamine and dimethylaniline, metallic sodium and an inert organic solvent such as toluene and xylene with stirring, suitably at about 50 – 70°C., to produce sodium methylacetylide in situ and adding carbon dioxide to the reaction mixture with stirring at 0 – 20°C. to produce sodium tetrolate. Sodium tetrolate is a known compound and useful, for example, as intermediate in the preparation of isoxazole derivatives.

4 Claims, No Drawings

PROCESS FOR PREPARING SODIUM TETROLATE

This is a continuation of application Ser. No. 376,934, filed July 6, 1973 which, in turn, was a Continuation application of Ser. No. 145,045, filed May 19, 1971 which, in turn, was a continuation application of Ser. No. 803,122, filed Feb. 27, 1969, all abandoned.

This invention relates to an improved process for preparing sodium tetrolate.

Sodium tetrolate is a known compound and useful, for example, as intermediate in the preparation of isoxazole derivatives (French Pat. No. 1,446,728). Heretofore, the process for preparing sodium tetrolate is disclosed in the Organic Synthesis, vol. 42, P. 97–100. According to the disclosure of said literature, sodium tetrolate is prepared by reacting methylacetylene with sodium amide in anhydrous liquid ammonia, evaporating the liquid ammonia from the reaction mixture and reacting sodium methylacetylide thus obtained with dry carbon dioxide in ether.

However, said process requires special equipments for a low temperature reaction and for recovery of the reaction medium because of employing liquid ammonia requires change of solvents on the way of process. Moreover, in carrying out the reaction of sodium acetylide with carbon dioxide, it requires a long time.

Further a process for preparing sodium acetylide is disclosed in the Journal of Organic Chemistry vol. 22, P. 649 (1957). According to the disclosure of the above literature, sodium acetylide is prepared by reacting acetylene with metallic sodium at 100°–110°C. in an inert organic solvent.

However, said process can not be satisfactorily applied to the preparation of sodium methylacetylide in a high yield and a high purity unless employing pure methylacetylene because of the production of by-products, since butadiene contained in raw methylacetylene tends to polymerize at 100°–110°C. with a catalytic action of metallic sodium.

Methylacetylene is commercially available as by-product in the preparation of butadiene from petroleum and, inevitably, contains a considerable amount of butadiene. Therefore, said process is commercially disadvantageous, in which raw methylacetylene containing butadiene can not be employed as a starting material. Furthermore, a process for preparing sodium tetrolate which comprises reacting sodium acetylide with carbon dioxide in the presence of an amido compound is disclosed in Japanese Pat. No. 481,274. However, in this prior process, when the amido compound is added to the reaction mixture obtained by reacting methylacetylene with metallic sodium for a continuous operation starting from methylacetylene, said amide compound reacts with the unreacted metallic sodium remaining in situ and thus it is necessary to prepare the starting sodium acetylide separately in a batchwise manner. Therefore, sodium tetrolate can not be continuously prepared from methylacetylene using the process mentioned above.

As a result of investigations for finding out a process for preparing sodium tetrolate from methylacetylene without disadvantages mentioned above, we have unexpectedly found that tertiary amines promote both a reaction of methylacetylene with metallic sodium and a reaction of sodium methylacetylide with carbon dioxide and also that they inhibit polymerization of butadiene contained in raw methylacetylene.

According to the present invention, sodium tetrolate is prepared by adding methylacetylene to a mixture of a tertiary amine, metallic sodium and an inert organic solvent (step 1) followed by adding carbon dioxide to the reaction mixture (step 2).

This process may be illustrated as follows:

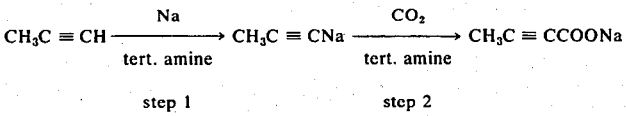

$$CH_3C \equiv CH \xrightarrow[\text{tert. amine}]{Na} CH_3C \equiv CNa \xrightarrow[\text{tert. amine}]{CO_2} CH_3C \equiv CCOONa$$

step 1          step 2

One of advantages of this invention is that the process for preparing sodium tetrolate from methylacetylene can be carried out with simple operations and equipments in short times. More particularly, the process does not require special equipments for low temperature and for recovery of a solvent. Furthermore, it can be continuously carried out, without change of solvents on the way of the process as required in the prior process.

Another advantage of this invention is that in the process raw methylacetylene containing butadiene can be employed as starting materials. As mentioned above, butadiene contained raw methylacetylene tends to polymerize at 100°–110°C. by a catalytic action of metallic sodium, which leads to a low purity and yield of sodium methylacetylide. However, according to the present invention, said polymerization is inhibited, because the process of this invention is carried out, suitably at 50°–70°C. and the tertiary amine has an inhibiting action for said polymerization itself. Therefore, raw methylacetylene containing butadiene can be satisfactorily employed in the process of this invention. In carrying out the step 1 of this invention, metallic sodium is dispersed into an inert organic solvent and then a tertiary amine is added to the mixture. Dry methylacetylene is then bubbled into the mixture thus obtained with stirring, suitably at about 50°–70°C. In carrying out the step 1, it is advantageous to previously replace air in a reaction vessel with methylacetylene or inert gas such as nitrogen gas or to pass a slow stream of said inert gas through the reaction vessel during the reaction. Immediately after dry methylacetylene is bubbled into the mixture, methylacetylene is absorbed and temperature of the reaction mixture begins to rise. The reaction temperatures are suitably kept at about 50°–70°C. by cooling. The rate and pressure of the bubbling can be properly selected by those skilled in the art. Step 1 is completed when the absorption of methylacetylene ceases and metallic sodium is completely exhausted to form a gray solid of sodium methylacetylide.

As the inert organic solvent used in the step 1 is suitably employed a solvent of hydrocarbon series, for example, benzene, toluene, xylene, hexane, heptane, petroleum benzin, ligroin and kerosene, but can be also employed other solvents which are inert to the reaction. The most suitable solvent is hydrocarbon such as xylene possessing higher boiling point than fusing point of sodium, because metallic sodium is advantageously dispersed with said hydrocarbon.

Examples of the tertiary amine used in this invention are aliphatic tertiary amine such as triethylamine, tri-n-propylamine, tri-n-butylamine, N,N,N',N'-tetramethylethylenediamine, N,N,N',N'-tetramethylpropylenediamine, aromatic tertiary amine such as N,N-dimethylaniline, N,N-diethylaniline and heterocyclic tertiary amine such as N-methylpiperidine, N,N'-dimethylpiperadine, N-methylmorpholine, N-ethylmorpholine, triethylenediamine. Triethylamine or dimethylamine is suitably used.

The tertiary amine is preferably employed at about 1–2 moles per mol of the metallic sodium, but less or more amounts than those mentioned above can be also employed.

The step 2 of this invention is suitably carried out by cooling the reaction mixture obtained by the step 1 to about 0°–20°C. and bubbling dry carbon dioxide into the reaction mixture. Immediately after dry carbon dioxide is bubbled into the mixture, carbon dioxide is absorbed and the temperature of the reaction mixture begins to rise. The reaction temperatures are suitably kept at about 0°–20°C. by cooling. The rate and pressure of the bubbling can be properly selected by those skilled in the art.

The step 2 is completed when the absorption of carbon dioxide ceases.

After completion of the step 2, sodium tetrolate may be isolated from the reaction mixture by one of the conventional methods, for example, by filtration or centrifugal separation.

The following examples are given by way of illustration only and as not limiting the scope of this invention.

EXAMPLE 1

23g. of metallic sodium is dispersed into 700ml. of xylene in a reaction vessel which is previously replaced with nitrogen gas and 202g. of triethylamine is added to the mixture.

The mixture thus obtained is heated to 56°C. and bubbled with dry methylacetylene at a rate of about 400ml./min. with stirring. Immediately after methylacetylene is bubbled, it is absorbed and the temperature of the reaction mixture begins to rise.

The methylacetylene is bubbled into the mixture at 60°C. for 80 minutes and metallic sodium in the mixture is completely exhausted to form a gray solid of sodium methylacetylide. The reaction mixture is cooled to about 10°C. and then bubbled with dry carbon dioxide. Immediately after carbon dioxide is bubbled, carbon dioxide is absorbed and the temperature of the reaction mixture rises to about 16°C.. While maintaining the above-mentioned condition, the bubbling of carbon dioxide is continued at a rate of about 700ml./min. for 80 minutes, during which period sodium methylacetylide is completely converted to sodium tetrolate. The mixture is subjected to suction filtration. The precipitates thus obtained are washed with xylene and dried in vacuum to give 105.0g. of the pure desired product as white micropowders.

EXAMPLE 2

11.5g. of metallic sodium is dispersed into 350ml. of xylene in a reaction vessel which is previously replaced with nitrogen gas and 60.5g. of N,N-dimethylaniline is added to the mixture. The mixture thus obtained is heated to about to 54°C. and bubbled with dry methylacetylene at a rate of about 150ml./min. with stirring for 90 minutes at about 60°C.

Then the reaction mixture is bubbled with dry carbon dioxide at a rate of about 450ml./min. for 50 minutes at about 12°–16°C.. After completion of the reaction, the reaction mixture is treated in same manner as shown in Example 1 to give 52.6g. of sodium tetrolate.

EXAMPLE 3

The process of Example 2 is followed, except that 50.5g. of N-methylmorpholine is substituted for 60.5g. of N,N-dimethylaniline to give 52.9g. of sodium tetrolate.

EXAMPLE 4

23g. of metallic sodium is dispersed into 800ml. of toluene in a reaction vessel which is previously replaced with nitrogen gas and 121g. of N,N-dimethylaniline is then added to the mixture. The mixture thus obtained is heated to about 56°C. and bubbled with a methylacetylene-butadiene (in a weight ratio of 1:4) mixture gas at a rate of about 1.35 l./min. for 100 minutes at about 60°C..

Then the reaction mixture is bubbled with dry carbon dioxide at a rate of about 650ml./min. for 80 minutes at about 12°–17°C..

After completion of the reaction, the reaction mixture is treated in the same manner as shown in Example 1 to give 105.6g. of sodium tetrolate.

What is claimed is:

1. In a process of preparing sodium tetrolate from methylacetylene, metallic sodium and carbon dioxide, the improvement which comprises introducing gaseous methylacetylene having a high content of butadiene into a mixture of tertiary amine, metallic sodium and a hydrocarbon solvent at a temperature ranging from 50° to 70°C, said tertiary amine being employed in an amount corresponding to about 1 to 2 moles per mole of said metallic sodium, and thereafter bubbling carbon dioxide into the reaction mixture at a temperature ranging from 0° to 20°C.

2. A process according to claim 1 wherein the tertiary amine is triethylamine.

3. A process according to claim 1 wherein the tertiary amine is dimethylaniline.

4. The process of claim 1, wherein the hydrocarbon solvent is xylene.

* * * * *